United States Patent [19]

Coggio et al.

[11] Patent Number: 5,734,085

[45] Date of Patent: Mar. 31, 1998

[54] FLUORINATED PHOSPHONIUM SALTS

[75] Inventors: William D. Coggio, Woodbury; Richard M. Flynn, Mahtomedi; George G. Moore, Afton, all of Minn.

[73] Assignee: Minnesota Mining and Manufacturing Company, St. Paul, Minn.

[21] Appl. No.: 576,708

[22] Filed: Dec. 21, 1995

[51] Int. Cl.$^6$ ........................................................ C07F 9/02
[52] U.S. Cl. ................................. 568/19; 568/11; 568/7
[58] Field of Search ............................................. 568/9, 11

[56] References Cited

U.S. PATENT DOCUMENTS

| | | | |
|---|---|---|---|
| 3,442,664 | 5/1969 | Heine | 106/2 |
| 3,518,292 | 6/1970 | Frye | 260/448.8 |
| 3,876,654 | 4/1975 | Pattison | 260/30.4 |
| 4,094,911 | 6/1978 | Mitsch et al. | 260/615 |
| 4,233,421 | 11/1980 | Worm | 525/343 |
| 4,259,463 | 3/1981 | Moggi et al. | 525/331 |
| 4,882,390 | 11/1989 | Grootaert et al. | 525/326.3 |
| 4,912,171 | 3/1990 | Grootaert et al. | 525/340 |
| 4,927,887 | 5/1990 | Tate et al. | 525/279 |
| 4,975,139 | 12/1990 | Sugimoto | 156/307.1 |
| 5,086,123 | 2/1992 | Guenthner et al. | 525/276 |
| 5,202,407 | 4/1993 | Pham et al. | 528/89 |
| 5,262,490 | 11/1993 | Kolb et al. | 525/343 |
| 5,274,159 | 12/1993 | Pellerite et al. | 556/485 |
| 5,322,904 | 6/1994 | Bierschenk et al. | 525/331.6 |
| 5,384,374 | 1/1995 | Guerra et al. | 525/326.4 |
| 5,424,438 | 6/1995 | Chittofrati et al. | 546/336 |

OTHER PUBLICATIONS

Brullo, R.A., "Fluoroelastomer Rubber for Automotive," *Automotive Elastomer & Design* (Jun. 1985).

Brullo, R.A., "Fluoroelastomer Seal Up Automotive Future," *Materials Engineering* (Oct. 1988).

Brullo, R.A., "Fluorocarbon Elastomers," *Encyclopedia of Polymer Science and Engineering*, vol. 7, pp. 256–269 (2d ed., John Wiley & Sons, 1987).

Rauhut et al., "The Free Radical Addition of Phosphines to Unsaturated Compounds", *Journal of Organic Chemistry*, vol. 26, pp. 5138–5145 (1961).

Pellon, "Reversibility in the Reaction of Phosphinyl Radicals with Olefins", *Journal of American Chemistry Society*, vol. 83, pp. 1915–1916 (1961).

Buckler et al., "Reactions of Phosphine with Aliphatic Aldehydes", *Journal of American Chemistry Society*, vol. 83, pp. 168–173 (1961).

Langhans et al., "Synthese Primärer und Sekundärer Phosphane Durch Selektive Alkylierung von PH$_3$ Unter Phasentransferbedingungen", *Z. Naturforsch*, vol. 45b, pp. 203–211 (1990).

Horváth et al., "Facile Catalyst Separation Without Water: Fluorous Biphase Hydroformylation of Olefins" *Science*, vol. 266, pp. 72–75 (1994).

*Primary Examiner*—Marianne M. Cintins
*Assistant Examiner*—Dwayne C. Jones
*Attorney, Agent, or Firm*—John A. Burtis

[57] ABSTRACT

A compound having the formula:

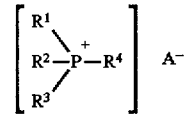

where $A^-$ is a counterion; $R^1$, $R^2$, $R^3$, and $R^4$, independently, comprise (a) a non-fluorinated alkyl, cycloalkyl, aryl, or aralkyl group; (b) an onium-containing group; or (c) a group having the formula $-(CH_2)_n-Y-R^5$ in which n is at least two; Y is a spacer arm comprising a $-CH_2-$, $-O-$, $-OCH_2-$, $-S-$, $-SO_2-$, or $-Z-SO_2-$ group; Z is an $-R^6-O-$, $-N(R^7)-$ group, or $-N(H)-$; $R^6$ is a substituted or unsubstituted phenylene group; $R^7$ is H or a non-fluorinated alkyl, cycloalkyl, aryl, or alkaryl group; and $R^5$ is a fluorinated group, perfluorinated group, or combination thereof, with the proviso that (i) at least one of $R^1$, $R^2$, $R^3$, and $R^4$ comprises a group having the formula $-(CH_2)_n-Y-R^5$; and (ii) the total number of fluorine atoms in said compound is at least 5.

The invention further includes curable compositions comprising vinylidene fluoride-containing polymers and the above-described compounds, as well as a method for curing such compositions.

13 Claims, No Drawings

FLUORINATED PHOSPHONIUM SALTS

FIELD OF THE INVENTION

This invention relates to fluorinated onium salts and to their use in curing vinylidene-fluoride-containing fluoropolymer compositions.

BACKGROUND

Fluoropolymers containing vinylidene fluoride units (e.g., copolymers of vinylidene fluoride and ethylenically unsaturated monomers such as hexafluoropropene) have particular utility in high temperature applications, including seals, gaskets, and linings, as described, for example, in Brullo, R. A., "Fluoroelastomer Rubber for Automotive Applications," *Automotive Elastomer & Design*, June 1985, "Fluoroelastomer Seal Up Automotive Future," *Materials Engineering*, October 1988, and "Fluorocarbon Elastomers," *Encyclopedia of Polymer Science and Engineering*, vol. 7, pp. 257 et seq. (2d ed., John Wiley & Sons, 1987). One reason is that such fluoropolymers, when cured, have good resistance to damage by heat, solvents, corrosive chemicals, and steam. However, the curing process is generally very slow, necessitating the use of a cure accelerator. A variety of organo-onium compounds have been proposed for this purpose.

In addition, during the manufacturing process (particularly where injection molding is used) the cured polymers generally adhere to the surface of the mold. As a result, a shaped article prepared from the fluoropolymer is frequently torn or damaged when removed from the mold. Also, the incorporation of a mold release agent into the polymer can have serious adverse effects on the physical properties of the cured composition (e.g., Mooney Scorch, shrinkage, and compression set) which can limit the successful commercial use of the cured composition. Deposits of polymer on the mold cavity surface ("mold fouling") and poor release of the shaped, cured article from the mold are major reasons for defects, resulting in rejection of the article (which then adds to the expense of manufacturing such articles).

One possible solution to the mold release problem is proposed in Kolb et at., U.S. Pat. No. 5,262,490 (which is hereby incorporated by reference). Kolb describes compositions containing a phosphonium or ammonium salt, a sulfonium compound, and (optionally) a polyhydroxy compound that are designed to perform the dual functions of accelerating fluoropolymer cure and providing mold release properties.

SUMMARY OF THE INVENTION

In general, the invention features a novel class of compounds useful, e.g., as cure accelerators for vinylidene fluoride-containing polymers having the formula:

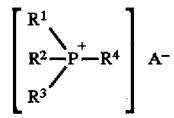 (1)

where $A^-$ is a counterion; $R^1$, $R^2$, $R^3$, and $R^4$, independently, comprise (a) a non-fluorinated alkyl (e.g., a branched or straight chain alkyl group such as methyl, ethyl, propyl, butyl, or iso-butyl), cycloalkyl (e.g., cyclohexyl), allyl, aryl (e.g., phenyl), or aralkyl (e.g., benzyl) group; (b) an onium-containing group; or (c) a group having the formula $-(CH_2)_n-Y-R^5$ in which n is at least two; Y is a spacer arm comprising a $-CH_2-$, $-O-$, $-OCH_2-$, $-S-$, $-SO_2-$, or $-Z-SO_2-$ group; Z is an $-R^6-O-$, $-N(R^7)-$, or $-N-(H)-$ group where $R^6$ is a substituted or unsubstituted phenylene group and $R^7$ is a non-fluorinated alkyl (e.g., a branched or straight chain $C_1-C_6$ alkyl group such as methyl), cycloalkyl (e.g., cyclohexyl), allyl, aryl (e.g., phenyl), or alkaryl group (e.g., benzyl); and $R^5$ is a fluorinated group, perfluorinated group, or combination thereof, with the proviso that (i) at least one of $R^1$, $R^2$, $R^3$, and $R^4$ comprises a group having the formula $-(CH_2)_n-Y-R^5$; and (ii) the total number of fluorine atoms in the compound is at least 5.

In preferred embodiments, at least one of the $R^1$, $R^2$, $R^3$, and $R^4$ groups comprises (1) an alkyl group having at least four carbon atoms; (2) a group having the formula $-(CH_2)_n-O-R^5$; or (3) a group having the formula $-(CH_2)_n-Ph-O-SO_2-R^5$ where Ph is a phenyl group. The $R^5$ group preferably is (1) a perfluorinated alkyl group; (2) a perfluorinated ether group having the formula:

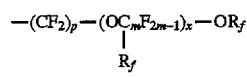

in which p is greater than or equal to zero with the proviso that when Y is $-O-$ p is greater than or equal to one, m is greater than or equal to one, x is greater than or equal to two, $R_f$ is a perfluoroalkyl group (e.g., a $C_1-C_6$ perfluorinated alkyl group such as a perfluorinated methyl group), and $R_{f'}$ is F or a perfluoroalkyl group (e.g., a $C_1-C_6$ perfluorinated alkyl group such as a perfluorinated methyl group); or (3) a fluorinated alkyl group having the formula $-CH_2-(CF_2)_x-H$ in which x is at least four.

One example of a preferred compound has the formula:

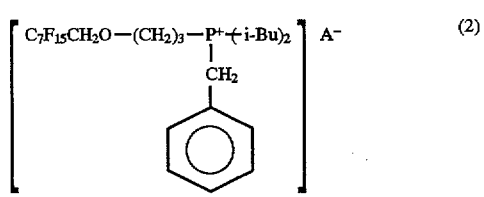 (2)

A second example of a preferred compound has the formula:

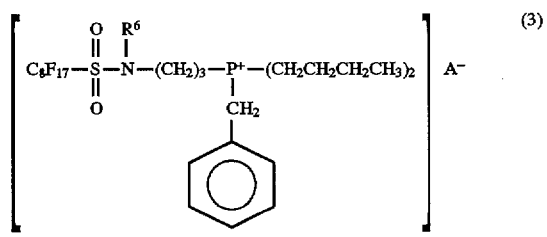 (3)

A third example of a preferred compound has the formula:

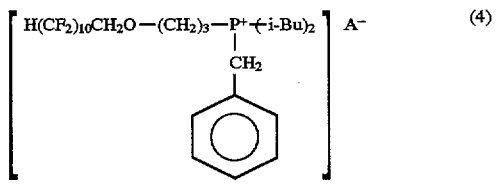 (4)

A fourth example of a preferred compound has the formula:

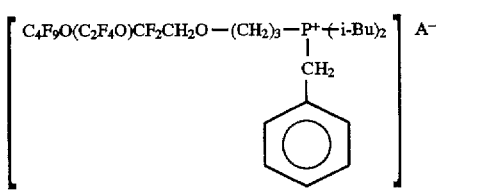

A fifth example of a preferred compound has the formula:

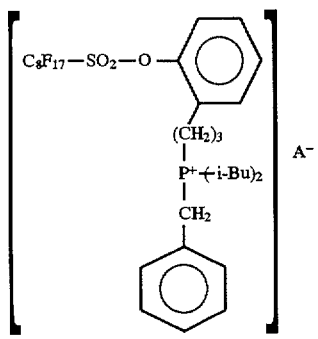

A sixth example of a preferred compound has the formula:

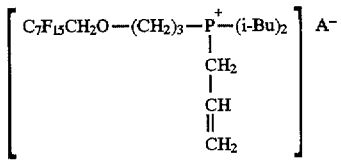

The invention also features a method of curing a polymer comprising vinylidene fluoride units using the above-described cure accelerators, as well as curable compositions comprising such polymers and the above-described cure accelerators. Preferably, cure is conducted in the absence of mold release agents.

As used herein:

A "mold release agent" refers to a material other than the cure accelerator that aids in removing the final cured composition from the mold in which cure takes place. Mold release agents include materials applied to the surface of the mold, as well as materials mixed together with the curable composition.

"Ph" refers to a phenyl group.

"i-Bu" refers to an isobutyl group

The invention provides curable compositions with rapid cure times in which cure time is decreased by means of a fluorinated onium cure accelerator. The fluorinated onium cure accelerator itself also provides good mold release properties, thereby dispensing with the need for separate mold release agents. The resulting cured articles exhibit good physical properties.

Other features and advantages of the invention will be apparent from the following description of the preferred embodiments thereof, and from the claims.

DESCRIPTION OF THE PREFERRED EMBODIMENTS

Curable vinylidene fluoride-containing fluoropolymer compositions according to the invention contain a fluorinated onium salt as a cure accelerator. Examples of preferred accelerators have the structures set forth in the Summary of the Invention, above, in which the counterion $A^-$ may be an organic or inorganic anion, e.g., halide, thiosulfate, formate, cyanate, thiocyanate, tetraphenylborate, perchlorate, nitrate, tetrafluoroborate, hexafluorophosphate, oxalate, stearate, haloacetate, para-toluenesulphonate, $ZnCl_4^{2-}$, $CdCl_4^{2-}$, $NiBr_4^{2-}$, $HgI_3^-$, sulfate, acetate, phosphate, phosphonate, hydroxide, alkoxide, phenoxide, trifluoromethane sulfonate, benzene sulfonate, hexachlorophosphate, hexachlorostannate, hexafluoroarsenate, hexafluoroantimonate, 2-mercaptobenzothiazolate, perfluoroalkanesulfonamido anion, bisphenoxide, or phenate. In cases where the counterion has a negative charge greater than one, a single counterion can be used for more than one onium compound.

The $R^1$ to $R^4$ and $R^6$ groups, independently, are preferably selected from the group of radicals consisting of alkyl, aryl, allyl, and alkenyl radicals, or combinations thereof. The R groups may be unsubstituted or substituted with one or more neutral, nonfunctional substituents that are non-ionizable under conditions of compounding or cure. Such substituents include, e.g., halogen atoms, cyano, —OR', and —COOR' moieties where R' is selected from the group of radicals consisting of $C_1$-$C_{20}$ alkyl, aryl, aralkyl, and alkenyl radicals. In addition, any pair of R groups can be connected with each other and the onium ion to form a heterocyclic ring.

The $R^5$ group is a fluorinated group, perfluorinated group, or combination thereof. Examples of preferred groups include fluorinated and perfluorinated alkyl and alkoxy groups.

The fluorinated onium salts are generally prepared by reacting, e.g., a phosphine with an alkylating agent, resulting in the expansion of the valence of the electron donating phosphorous atom and a positive charge on the organoonium.

Examples of curable vinylidene fluoride-containing polymers are described in the aforementioned Kolb patent; Worm, U.S. Pat. No. 4,233,421; and Grootaert et al., U.S. Pat. No. 4,882,390, all of which are hereby incorporated by reference. Specific examples include copolymers and terpolymers of vinylidene fluoride with terminally unsaturated monoolefins typically used for the preparation of fluorine-containing polymers such as hexafluoropropene, chlorotrifluoroethylene, 2-chloropentafluoropropene, perfluoroalkyl vinyl ethers (e.g., $CF_3OCF{=}CF_2$ or $CF_3CF_2OCF{=}CF_2$), tetrafluoroethylene, 1-hydropentafluoropropene, 2-hydropentafluoropropene, dichlorodifluoroethylene, trifluoroethylene, 1,1-dichlorofluoroethylene, vinyl fluoride, and mixtures thereof. Fluorine-free terminally unsaturated monoolefin monomers, e.g., ethylene or propylene, may also be used as co-monomers.

Fillers are often added to the polymers discussed above to improve the physical properties of the cured composition or vulcanizate. When a filler is employed, it is added to the vulcanization recipe in amounts of up to about 100 parts per hundred parts by weight of polymer, preferably between about 1 and 50 parts per hundred parts by weight of the polymer. Examples of fillers which may be used are reinforcing thermal grade carbon blacks or non-black pigments of relatively low reinforcement characteristics such as clays, barytes, etc. In some instances, it may also be desirable to add one or more diorgano sulfur oxide compounds, and other conventional adjuvants or ingredients, e.g., retarding agents and processing aids to the curable composition.

The curable composition preferably contains a crosslinking agent as well. Such agents are well known and are described in the art, e.g., in the aforementioned Kolb and Worm patents, and in U.S. Pat. Nos. 4,259,463 (Moggi et at.), 3,876,654 (Pattison), and 5,384,374 (Guerra et al.), all of which are hereby incorporated by reference, and can include aromatic polyhydroxy compounds, aliphatic polyhydroxy compounds, and derivatives thereof. Blends may be used as well. Preferred polyhydroxy compounds are aromatic polyhydroxy compounds such as isopropylidene-bis (4-hydroxy-benzene) ("bisphenol A") and hexafluoroisopropylidenebis(4-hydroxybenzene) ("bisphenol AF").

Fluoroaliphatic sulfonamides can also be added, including those of the formula $R_fSO_2NHR''$, where $R''$ is a hydrogen atom or alkyl radical having, for example, from 1 to 20 carbon atoms, preferably from 1 to 12 carbon atoms, $R_f$ is a fluoroaliphatic radical such as a perfluoroalkyl, e.g., $C_nF_{2n+1}$ where n is 1 to 20, or perfluorocycloalkyl, e.g., $C_nF_{2n-1}$ where n is 3 to 20, such compounds being described, for example, in U.S. Pat. No. 5,086,123 (Guenther et al.). The fluoroaliphatic sulfonamide is preferably a perfluoroalkyl-sulfonamide and may be added as a separate compound, or as the anion of the organo-onium compound.

The fluorinated cure accelerators and crosslinking agent can be added to the uncured polymer gum in the form of finely divided solids or as solutions in alcohol or ketone solvents by mixing the materials into the polymer gum stock. Thus mixed, the gum stock can generally be stored at room temperature for extended periods, e.g., up to two years or more.

Prior to curing, an acid acceptor is mixed into the gum stock, after which storage life of the stock is more limited. Acid acceptors can be inorganic or organic. Organic acceptors include epoxies, sodium stearate, and magnesium oxalate. Examples of inorganic acceptors include magnesium oxide, lead oxide, calcium oxide, calcium hydroxide, dibasic lead phosphite, zinc oxide, barium carbonate, strontium hydroxide, calcium carbonate, etc. The preferred acid acceptors are magnesium oxide and calcium hydroxide. The acid acceptors can be used singly or in combination, and preferably are used in amounts ranging from about 2 to 25 parts per 100 parts by weight of the polymer. All of the components of the curing system may be admixed prior to their incorporation into the polymer gum without departing from the scope of the invention.

The relative amounts of the crosslinking agent and fluorinated onium salt are present in the composition in such amounts as to provide the desired cure and/or mold release of the composition when mixed with acid acceptor. Representative proportions of components of the curing system are as follows:

Acid acceptor: 0.5 to 40 phr
Onium salt: 0.2 to 5 mmhr
Crosslinker: 0.3 to 10 mmhr All amounts are given in parts per 100 parts polymer (abbreviated "phr") or in millimoles per hundred grams polymer (abbreviated "mmhr"). These proportions are general ranges. The particular amount for each particular cure time and temperature will be apparent to one of ordinary skill in the art.

In accordance with this invention, the desired amount of acid acceptor, fluorinated onium salt, crosslinking agent, diorgano sulfur oxide compounds (if any), and other conventional adjuvants or ingredients are added to the unvulcanized polymer (i.e. gum stock) and intimately admixed therewith or compounded by employing any of the usual rubber mixing devices such as Banbury mixers, roll mills, or any other convenient mixing device. For best results the temperature of the composition during mixing should not rise above about 120° C. During mixing it is necessary to distribute the components and adjuvants uniformly throughout the curable polymer.

The curing process typically comprises molding the resulting composition under pressure at a temperature ranging from about 95° C. to about 230° C., followed by curing. The composition of this invention is particularly useful for injection molding. The molded product is then usually post cured (e.g., oven cured) at a temperature between about 150° C. and about 315° C., usually at about 232° C., for a period of from about 2 hours to 50 hours or more depending on the cross-sectional thickness of the sample.

The invention will now be further described by way of the following examples.

EXAMPLES

Samples of fluorinated phosphonium cure accelerators of the present invention and curable compositions comprising such oniums were prepared as described below. The reactions were carried out at room temperature and pressures unless otherwise noted. Percentages listed are weight percent unless otherwise noted. Structural characterization data were obtained by NMR, IR spectroscopic techniques.

The precursor fluoroalkyl phosphines used for the preparation of cure accelerators according to the invention were prepared via free radical hydrophosphorylation reaction between diisobutylphosphine (DIBP) and a fluoroalkyl allyl ether or an allyl fluorosulfonamide. Such hydrophosphorylation reactions are well-known in the art. The teachings of Rahut, M. M. et al *J. Org. Chem.*, 1961, 26, 5138; Pellon, J, *J. Am Chem .Soc.*, 1961, 83, 1915; Buckler, S. A., et al, *J. Am Chem .Soc.*, 1961, 83, 168; Langhans, K. P., et al *Z Naturforsch* 1990, 45b, 203 and Horvath, I. T. et al *Science*, 1994, 266, 72 are typical of a great many examples of this type of reaction. Subsequent quaternary phosphonium salts were prepared from these phosphines by interaction of the phosphine with an alkyl, allyl, or benzyl halide.

Comparative Examples of fluoroalkyl amide phosphonium cure accelerators were prepared via a transamidation reaction between 3-aminopropyl diisobutyl phosphine and methyl perfluoro alkyl esters. The reactions were carried out at 0° C. without solvent, followed by quaternization with an alkyl or benzyl halide. 3-aminopropyl diisobutylphosphine was prepared by a hydrophosphorylation between DIBP and allyl amine in similar fashion to hydrophosphorylation reactions described previously. The methyl perfluoro esters were prepared as described in U.S. Pat. Nos. 5,362,919 (Costello et al.), 5,322,904 (Bierschenk et al.), and 4,094,911 (Mitsch et al.).

Cure and rheological properties of curable compositions and physical properties of cured sheets were evaluated using the following test methods:

Cure Rheology Tests were run on uncured, compounded admixtures using a Monsanto Moving Die Rheometer (MDR) Model 2000E at 177° C. on an 8.0 g quantity of the admixture in accordance with ASTM D 5289-93a for a rotorless rheometer, no preheat, an oscillator frequency of 100 cpm and a 0.5° arc. Minimum torque ($M_L$), maximum torque ($M_H$), and delta torque ($\Delta T$), the difference between $M_H$ and $M_L$, were reported. Also reported were $t_s2$ (the time to a 2 unit rise in torque from $M_L$), t'50 (the time to increase torque above $M_L$ by 50% of delta torque), and t'90 (the time to increase torque above $M_L$ by 90% of delta torque), all of which were reported in minutes.

Physical properties were tested on samples cut from press-cured and post-cured sheets. Press-Cure data, unless otherwise noted, were obtained from 20×20×0.2 cm sheets prepared by pressing a sample of the curable compositions at about 6.9 MPa for 10 min. at 177° C. Post-Cure data were obtained from sheets prepared as described above which were then further treated or cured by heating the sheets in a circulating air oven maintained at about 232° C. for 16 hours.

Tensile strength at break, elongation at break and stress at 100% elongation were determined using a Monsanto mechanical tester with a 200 lb (88.9 kg) load cell in accordance with ASTM D 412-92$^{s1}$. Test specimens were cut from the press- or post-cured sheets using Die D. A 1" (25.4 mm) gage section was used to follow the cross head displacement. All tests were run at a constant crosshead displacement rate of 20"/minute (508 mm/min.) in triplicate. The values reported were averages of the three tests. Stress at 100% elongation, elongation at break, and tensile strength at break were reported in units of mega Pascals (MPa), %, and MPa, respectively.

Evaluations of injection molding performance, i.e. mold release, were performed using a DESMA 966.053 ZO lab injection molding machine available from Kloeckner Ferromatic Desma Gmbh of Germany. The machine is further described as having 500 kN mold closing force, 27 kW total power installed, 55 mm injection piston diameter, 120 mm maximum piston stroke, 200 MPa maximum injection pressure, 400 mm/sec. maximum injection speed and a plastication unit with 30 mm screw diameter and screw RPM of 30–220. The mold used to make O-rings was a 4 cavity mold with O-ring internal diameter of 48 mm, O-ring cross-section of 2.90 mm, a runner length of 13 mm, sprue base diameter of 5.2 mm, sprue length of 29 mm, and each cavity had a vacuum canal. The mold steel was STAVAX ESR with a surface finish EDM.

The mold was conditioned before each experiment (change of formulation) by blasting the mold surface with 50–150 micron glass beads under 0.2 MPa pressure for 10 minutes. The mold was then conditioned for 30 minutes in a water-based caustic solution at 80° C. and then ultrasonically cleaned in the solution for 10 minutes. After cleaning, the mold was rinsed with deionized water, dried and stored overnight before use. Multiple molding cycles were made of each formulation.

The steady state O-ring injection molding conditions were 190° C. mold temperature, 95° C. injection barrel temperature, 60° C. screw barrel temperature, injection speed 60% of maximum, after-injection pressure of 5.5 MPa for 2 seconds, screw RPM 35% of maximum, backpressure of 0.5 MPa, plastication delay of 2 seconds after end holding time and a vacuum time of 2.5 seconds. The holding time and heating time were both dependent upon vulcanization speed and were adjusted to obtain cured O-rings. The shot size was adjusted to give similar flash to the parts molded.

Injection Molding Evaluations were performed as described above and evaluated with the following rating system ranging from a rating of 0 (worst release) to a rating of 8 (best release):

A release rating of 0 was given:
When no parts could be removed from the mold by any means without tearing them and this was observed for each molding cycle. The molded parts may or may not have torn when the mold was opened. Everything including runners and flash stuck strongly to the mold surface and was difficult to remove. Rubbing with copper wool or similar was needed to remove any stuck flash or molded goods from the mold surface.

A release rating of 1 was given:
When only some of the parts could be removed in one piece, although with great difficulty even when demolding was assisted with an air gun. The molded parts may or may not have torn when the mold was opened. Everything including runners and flash stuck strongly to the mold surface and was difficult to remove. Rubbing with copper wool or similar was needed to remove any stuck flash or molded goods from the mold surface.

A release rating of 2 was given:
When most of the parts could be removed in one piece, although with great difficulty even when demolding was assisted with an air gun. Everything including runners and flash stuck strongly to the mold surface and was difficult to remove. Rubbing with copper wool or similar was needed to remove any stuck flash or molded goods from the mold surface. Air alone was not enough to demold the stuck parts or flash.

A release rating of 3 was given:
When nearly all parts could be removed in one piece, but only with the assistance of an air gun. The runners and some flash could be removed with the air gun but not without tearing. The remaining flash that stuck to the mold required rubbing with fabric to remove it from the mold. Air alone was not enough.

A release rating of 4 was given:
When all parts could be removed in one piece, but only with the assistance of an air gun. The runners could be removed without tearing but not in one piece with the parts, even when assisted with an air gun. A lot of flash tore and stuck to the mold and required rubbing with fabric to remove it from the mold. Air alone was not enough.

A release rating of 5 was given:
When all parts and runner system could be removed without tearing, but only with the assistance of an air gun. Some flash tore and stuck to the mold and required rubbing with fabric to remove it from the mold. Air alone was not enough to remove flash that remained stuck to the mold surface.

A release rating of 6 was given:
When nearly all parts and runner system could be removed without tearing, but only with the assistance of an air gun. Flash seldom tore and stuck to the mold. When some flash did stick to the mold, light rubbing or a short blast from the air gun easily removed the flash.

A release rating of 7 was given:
When all shots, parts, runner system and flash could be removed without tearing, but only minimal assistance of an air gun was used. Occasional demolding without air and tearing was possible.

A release rating of 8 was given:
When all parts, runners and flash could be consistently removed without tearing and without using air. Demolding by hand and with very low forces was all that was required to removed all parts, runners and flash.

FLUORINATED PHOSPHONIUM CURE ACCELERATORS

Precursor fluoroalkyl phosphines used in the preparation of the fluorinated phosphonium cure accelerators of the invention were prepared as described below.

Phosphine A 3-(1,1-dihydroperfluorooctyloxy)propyl diisobutylphosphine (Phosphine A) was prepared in a 1000 mL, 4 neck flask, equipped with an overhead stirrer, a condenser, nitrogen purge adapter, thermometer and rubber septum by charging 170 g of a 70% solids solution in toluene (0.82 mol) of diisobutyl phosphine (DIBP), available from Cytec Industries, Inc. The flask assembly was placed on an adjustable lab jack so that either external heating or cooling of the reaction flask could be done. Additional toluene was added to dilute the DIBP solution to about 50% solids. The reaction flask was purged with nitrogen for fifteen minutes and a positive stream of nitrogen was maintained through the reaction flask to minimize the oxidation of the DIBP.

In a second flask, 351 g (0.84 mol) of 1,1-dihydroperfluoro octyl allyl ether, ($CF_3(CF_2)_6CH_2O$—$CH_2$—$CH=CH_2$), prepared as described in Ex. 1 of U.S. Pat. No. 5,274,159 (Pellerite et al.), was mixed with about 100 ml of toluene and 1.3 g (8.5 mmol) of azobisisobutyronitrile (AIBN), available from Aldrich Chemical Company, Inc. The toluene solution of DIBP was warmed to about 80° C. and the allyl ether solution in the second flask was added to the warm DIBP at about 2.5 mL/min. via a syringe pump. After about 20 min., a noticeable exotherm was detected and the rate of allyl ether addition and external heating was adjusted so that a temperature of 80° to 95° C. could be maintained. After complete addition of the allyl ether solution, the reaction mixture was heated to 85° C. for an additional 2 hrs to ensure complete consumption of the DIBP had occurred.

When the reaction was complete as determined by $^{31}P$ NMR spectroscopy ($\delta$=−40 ppm up field from external $H_3PO_4$ for the trialkyl phosphine product), the toluene solvent was removed under reduced pressure. $^1H$, $^{31}P$ NMR spectroscopy confirmed the structure to be that of the desired product 3-(1,1-dihydroperfluorooctyloxy) propyl diisobutylphosphine.

Phosphine B 3-(1,1-dihydroperfluoropropoxy) propyl diisobutylphosphine (Phosphine B) was prepared in a three neck round bottomed flask equipped with a magnetic stir bar, reflux condenser, addition funnel and a nitrogen purge inlet by charging 28.3 g (1.23 mol) Sodium metal and then adding 500 ml of dry tetrahydrofuran to disperse the sodium metal. The addition funnel was charged with a solution of dry THF in which was dissolved 188 g (1.25 mol) of pentafluoropropanol, available from Aldrich Chemical Company, Inc. The pentafluoropropanol solution was added slowly to the sodium metal at a rate sufficient enough to maintain a reaction temperature of about 40° to 50° C.

Upon complete consumption of the sodium metal, a solution of 188 g (1.57 mol) allyl bromide, available from Aldrich Chemical Company, Inc., in about 200 ml of THF was added slowly. The formation of precipitated NaBr was observed in the reaction flask during the addition. After complete addition of the allyl bromide solution, the reaction mixture was refluxed for an additional 12 hrs. The reaction mixture was allowed to cool to room temperature (about 24° C.) and the NaBr precipitate was removed by filtration.

The THF solution was poured into 2 L of deionized water made alkaline by the addition of 10 g of KOH. The lower product layer was separated and washed three more times in this fashion. The product layer was dried using $MgSO_4$, filtered and distilled. The desired product was isolated by distillation, b.p. (72°–82° C.). $^{19}F$, $^1H$ NMR spectroscopy confirmed the structure of the product as 1,1-Dihydropentafluoropropyl allyl ether ($CF_3CF_2CH_2O$—$CH_2$—$CH=CH_2$). Product contained 3% w/w THF as determined by $^1H$ NMR spectroscopy. The 3-(1,1-dihydroperfluoropropoxy) propyl diisobutylphosphine was then prepared in a manner similar to the preparation described for Phosphine A except that 3-(1,1-dihydropentafluoropropyl) allyl ether was used in the hydrophosphorylation reaction.

Phosphine C

Bis(3-(1,1-dihydroperfluoropropoxy)propyl)isobutyl phosphine (Phosphine C) was prepared in manner similar to that used for the preparation of Phosphine A except that the reaction stoichiometry was adjusted so that two equivalents of 1,1-dihydroperfluoropropyl allyl ether, ($CF_3CF_2CH_2O$—$CH_2$—$CH=CH_2$), were allowed to react with one equivalent of isobutyl phosphine ($H_2$—P-iBu).

Phosphine D

N-ethyl, N-(3-diisobutyl phosphino)propyl perfluoro octane sulfonamide (Phosphine D) was prepared in a manner similar to Phosphine A except N-ethyl, N-allyl perfluorooctane sulfonamide, ($C_8F_{17}SO_2$—N(Et)—$CH_2CH=CH_2$), prepared according to Example 7 of U.S. Pat. No. 3,442,664 (Heine), was used. In preparing Phosphine D, the starting allyl sulfonamide was not completely consumed by the DIBP after 60 hrs at 100° C. A $^{31}P$ NMR spectrum of the reaction mixture after 60 hrs of reaction time showed that approximately 35% of the desired phosphine formed.

The flask was charged with 38 g (0.26 mol) of DIBP. A toluene solution containing 160 g (0.28 mol) of $C_8F_{17}SO_2$—N(Et)—$CH_2CH=CH_2$ and 5 mol % AIBN was added via syringe pump over a 3 hr period. No noticeable exotherm was noted and the reaction mixture temperature was increased to 100° C. The reaction mixture was heated at this temperature for an additional 60 hrs. The progress of the reaction was monitored by gas chromatography and $^{31}P$ NMR spectroscopy. After this time period, the toluene solvent and unreacted DIBP were removed by simple distillation under reduced pressure (40° to 80° C. @ 1 mmHg). The remaining mixture of the desired product and unreacted $C_8F_{17}SO_2$—N(Et)—$CH_2CH=CH_2$ were transferred to a 200 mL, one neck, round bottomed flask. The allyl sulfonamide starting material was removed by Kugelrohr distillation at 140° to 150° C. at 1 mm Hg to yield the desired product. $^{31}P$, $^{19}F$ and $^1H$ confirmed the formation of the desired product, N-ethyl, N-(3-diisobutyl phosphino)propyl perfluoro octane sulfonamide, $C_8F_{17}SO_2$—N(Et)—$(CH_2)_3$—P—$(i-Bu)_2$. $^1H$ NMR spectroscopy suggested that the product contained less than 1 wt % of unreacted $C_8F_{17}SO_2$—N(Et)—$CH_2CH=CH_2$.

Example 1

In Example 1, a fluorinated phosphonium cure accelerator of the present invention was prepared in a 200 ml airless flask equipped with a nitrogen purge inlet and a magnetic stir bar by charging 50 g (0.085 mol) of Phosphine A [3-(1,1-dihydroperfluorooctyloxy)propyl diisobutylphosphine] to the flask. Next, 20 ml of 2-propanol was added to the flask to dissolve Phosphine A, and 10.8 g of benzyl chloride (0.085 mol), available from Aldrich Chemical Co., was added to the phosphine solution. The resulting mixture was heated to about 50° C. for 12 hrs. $^{31}P$ NMR spectroscopy of the reaction mixture showed that the phosphine had been quantitatively converted to the trialkyl benzyl phosphonium halide. $^{31}P$ NMR chemical shift data for the starting phosphine is at $\delta$=−40 ppm, whereas the phosphonium chemical shift is observed in the region of $\delta$=+32 ppm. The 2-propanol was removed under vacuum and the product (3-(1,1- dihydroperfluorooctyloxy)propyl diisobutyl benzyl phosphonium chloride) was dried further under vacuum for about 12 hrs at 50 C. $^1$H, $^{31}$P and $^{19}$F NMR spectra confirmed the structure of the desired product.

Examples 2–4

In Examples 2–4, fluorinated phosphonium cure accelerators of the invention were made in a manner similar to Example 1 except Phosphine B was used in Example 2 instead of Phosphine A. Phosphine C was used in Example 3, and Phosphine D was used in Example 4.

Example 5

2-((3-diisobutyl benzyl phosphonium chloride)propyl) phenyl perfluorooctane sulfonate was made by first preparing 3-(2-hydroxyl phenyl)propyl diisobutyl phosphine in a manner similar to Phosphine A except using 2-allyl phenol and DIBP. A 3-neck reaction vessel equipped with condenser, mechanical stirrer and an addition funnel was then charged with 3.6 g (0.09 mol) of NaH, 60% dispersion in mineral oil, and 350 mL of dry THF.

In a separate flask, 25.0 g (0.09 mol) of the 3-[2-hydroxy phenyl]propyl diisobutyl phosphine above was dissolved in 50 mL of THF. This phosphine solution was added slowly to the NaH dispersion at room temperature. After consumption of the NaH, determined by lack of H$_2$ gas evolution, a solution of 44.5 g (0.09 mol) of Fluorad™ perfluorooctane sulfonyl fluoride FX-8, available from 3M Co. of St. Paul, Minn., in 100 mL of Fluorinert™ Electronic Liquid FC-72, also available from 3M Co., was added drop wise to the phosphine solution. The resulting mixture was then heated to reflux (about 45° C.) for 16 hrs. The reaction was followed by $^{19}$F NMR spectroscopy and was considered complete when the sulfonyl fluoride signal at +40 ppm downfield from CFCl$_3$ was no longer detected in the NMR spectrum.

The reaction mixture was worked up by extraction of the product mixture with water and methylene chloride. The organic layers were combined and dried with MgSO$_4$ and the solvent was removed under reduced pressure. The product was isolated as a viscous, light brown oil, 61.6 g (88% yield). Characterization by $^1$H, $^{31}$P, $^{19}$F NMR spectroscopy confirmed the proper structure of the product.

In a separate flask, 51.3 g (0.072 mol) of the resulting phosphine intermediate, 2-(propyl(3-diisobutyl phosphine)) phenyl perfluorooctane sulfonate, was dissolved in about 50 ml 2-propanol. To this mixture, 9.0 g (0.071 mol) of benzyl chloride was added and the reaction mixture was warmed to about 50° C. for 16 hrs. The desired product was obtained by removing the solvent from the reaction mixture and drying the product under vacuum.

Example 6

The preparation of 3-(1,1-dihydroperfluorooctyloxy) propyl diisobutyl allyl phosphonium chloride was carried out in a manner similar to the synthesis of the phosphonium listed in Example 1. In this procedure, the starting phosphine A (50.0 g, 0.085 mol) was dissolved in 40 g of ethanol. This solution was then mixed with 8.5 g (0.112 mol, 1.3 molar excess) of allyl chloride (available from Aldrich Chemical Co.). The reaction mixture was heated to 45° C. for 12 hours. The conversion of phosphine A to the desired phosphonium was monitored by $^{31}$P NMR spectroscopy. The phosphonium product was isolated by removal of the solvent by rotoevaporation followed by further drying under vacuum at room temperature. The product 3-(1,1-dihydroperfluorooctyloxy)propyl diisobutyl allyl phosphonium chloride, was isolated as a light orange, viscous oil in about 80 to 90% yield.

CURABLE COMPOSITIONS

The ingredients used in each curable composition were mixed on a two-roll mill using standard methods. The polyhydroxy crosslinking agent, 4,4'-(hexafluoroisopropylidene) diphenol (bisphenol AF), and calcium hydroxide are commercially available from Aldrich Chemical Company, Inc. Magnesium oxide is available as "Maglite D," and carbon black is available as "Thermax MT, ASTM N990." Amounts of the reagents are listed in parts per hundred rubber, (pphr) or mmoles per hundred parts rubber, (mmhr).

Example 7

In Example 7, a curable composition of the invention was prepared by mixing the following ingredients together on a conventional two-roll mill using standard methods: 100 g of a fluorine-containing copolymer of vinylidene fluoride (60 wt %) and hexafluoropropylene (40 wt %), available from 3M Co. as Fluorel™ Fluoroelastomer FC-2145, 2.1 g (6.1 mmol) of bisphenol-AF and a methanol solution (about 50% solids) of 0.92 g (1.29 mmhr) of the fluorinated onium cure accelerator prepared above as Example 1. Next, 6 g of Ca(OH)$_2$, 3 g of MgO and 30 g of carbon black were added to the composition being milled. After additional mixing to ensure a homogenous mixture, the cure properties of the resulting curable composition were analyzed using a Monsanto Moving Die Rheometer at 177° C. for 12 minutes. The results are reported in Table 1.

A press-cured sheet was prepared by pressing a quantity of the curable composition at about 6.9 MPa at 177° C. for 10 minutes. The resulting press-cured sheet was evaluated for physical properties. A sample of the press-cured sheet was further treated or cured for 16 hours at 232° C., resulting in a post-cured sheet which was also evaluated for physical properties. The press-cured and post-cured sheet test results are reported in Tables 2 and 3.

Examples 8–11

In Examples 8–11, curable compositions of the invention were prepared and evaluated in a manner similar to Example 7 except the fluorinated onium cure accelerator used was varied as follows: Example 8 used the compound prepared above as Example 2, Example 9 was prepared using the compound prepared above as Example 3, Example 10 was prepared using the compound prepared above as Example 4, and Example 11 was prepared using the compound prepared above as Example 5. Data are reported in Tables 1–4.

Example 12

The curable fluoroelastomer composition of Example 12 was prepared and evaluated in a manner similar to Example 7 except the fluorinated onium cure accelerator used was varied as follows: the phosphonium compound described in Example 6 was used and 0.662 phr (1 mmhr) of onium was used instead of 1.29 mmhr. Data are reported in Tables 1–5.

Comparative Examples C1–C3

In Comparative Example C1, a curable composition was prepared and evaluated as in Example 7 except the onium cure accelerator used was benzyltriphenyl phosphonium chloride, a commonly used cure accelerator commercially available from Aldrich Chemical Company, Inc.

In Comparative Example C2, a curable composition was prepared and evaluated as in Example 7 except the onium cure accelerator used, N-3-(diisobutyl benzyl phosphonium chloride) propyl perfluorooctanoic acid amide, was prepared in a one neck, airless flask, equipped with a magnetic stir bar, a nitrogen inlet adapter and a rubber septum into which was charged 28.5 g (0.067 mol) of methyl perfluorooctanoate, available from PCR Corp. The perfluorooctanoate was cooled to 0° C., and 12.8 g (0.063 mol) of 3-aminopropyl diisobutylphosphine was added via a syringe. The resulting mixture was stirred at 0° C. for 1 to 1.5 hrs. An infrared spectrum of the reaction mixture showed that the methyl ester carbonyl stretch at 1790 $cm^{-1}$ was absent and a new carbonyl stretch at 1700 to 1710 $cm^{-1}$ was present. In addition, a gas chromatograph of the product mixture confirmed that one new product had formed.

The reaction mixture was warmed to about 45° C., diluted to about 50% solids with methanol and then 7.9 g (0.063 mol) of benzyl chloride was added and the reaction was continued for 12 hrs. A $^{31}P$ NMR spectrum of the reaction mixture consisted of only a singlet at +30 ppm suggesting that complete consumption of the phosphine had occurred. The product, a highly viscous, light brown oil, was isolated by solvent removal and drying the product under vacuum. The product was characterized by P, $^1H$ and $^{19}F$ NMR spectroscopy.

In Comparative Example C3, a curable composition was prepared and evaluated as in Example 7 except the onium cure accelerator used was prepared in a manner similar to the onium cure accelerator in Comparative Example C2 except methyl perfluoro butoxy ethoxy ethanoate was used instead of methyl perfluorooctanoate.

Data for the comparative examples are reported in Tables 1–4.

TABLE 1

| Example | $M_L$ (dN·m) | Torque $M_H$ (dN·m) | ΔT (dN·m) | $t_s2$ (min.) | t'50 (min.) | t'90 (min.) |
|---|---|---|---|---|---|---|
| 7 | 0.86 | 24.40 | 23.5 | 0.67 | 0.86 | 1.82 |
| 8 | 0.80 | 27.0 | 26.2 | 1.54 | 1.96 | 2.62 |
| 9 | 0.80 | 25.9 | 25.1 | 1.45 | 1.94 | 2.67 |
| 10 | 0.50 | 23.7 | 23.2 | 1.04 | 1.41 | 1.95 |
| 11 | 0.75 | 23.0 | 22.3 | 0.93 | 1.21 | 1.71 |
| 12 | 0.81 | 27.5 | 26.8 | 0.82 | 1.02 | 1.30 |
| C1 | 0.84 | 26.3 | 25.4 | 1.89 | 2.35 | 3.27 |
| C2 | 0.70 | 23.7 | 23.0 | 1.44 | 1.97 | 2.76 |
| C3 | 0.67 | 23.4 | 22.7 | 1.08 | 1.38 | 2.06 |

The data in Table 1 indicate a more rapid cure when using onium cure accelerators of the present invention as compared to Comparative Example C1, the non-fluorinated onium.

TABLE 2

Press-Cured Sheet Mechanical Property Data

| Example | Stress at 100% Elong. (MPa) | Elongation at Break (%) | Tensile Strength (MPa) |
|---|---|---|---|
| 7 | 4.9 | 216 | 8.7 |
| 8 | 4.4 | 232 | 8.6 |
| 9 | 4.5 | 220 | 8.5 |
| 10 | 3.6 | 224 | 8.5 |
| 11 | 4.6 | 279 | 8.2 |
| 12 | 6.3 | 199 | 9.3 |
| C1 | 4.3 | 244 | 8.4 |
| C2 | 4.4 | 216 | 7.9 |
| C3 | 4.4 | 205 | 8.0 |

The results in Table 2 show that the curable compositions of this invention provide cured articles with acceptable initial cure properties.

TABLE 3

Post-Cure Sheet Mechanical Property Data

| Example | Stress at 100% Elong. (MPa) | Elongation at Break (%) | Tensile Strength (MPa) |
|---|---|---|---|
| 7 | 7.7 | 165 | 13.9 |
| 8 | 7.0 | 183 | 14.3 |
| 9 | 6.9 | 181 | 14.3 |
| 10 | 5.2 | 213 | 13.1 |
| 11 | 7.2 | 170 | 13.1 |
| 12 | 7.5 | 163 | 14.9 |
| C1 | 5.8 | 199 | 13.1 |
| C2 | 8.1 | 164 | 14.4 |
| C3 | 8.3 | 143 | 12.7 |

The results in Table 3 show the curable compositions of this invention provide cured articles with acceptable post cure properties.

Compression set data were obtained using ASTM method D-395-89. O-rings were press cured for 12 min. at 177° C. and post cured for 16 hrs at 232° C. O-rings were compressed 25% for 70 hrs at 200° C. Data (shown in Table 4) are reported as percent of the compression remaining after the tests.

TABLE 4

| Example | Comp set (%) |
|---|---|
| 7 | 19.6 |
| 8 | 21.5 |
| 9 | 21.0 |
| 10 | 22.0 |
| 11 | 24.0 |
| 12 | 15.8 |
| C1 | 18.0 |
| C2 | 35.0 |
| C3 | 35.0 |

The results in Table 4 show the curable compositions of this invention provide cured articles with compression set properties which are superior to Comparative Examples C2 and C3.

Examples 13

In Example 13, a curable composition of the invention was made in a manner similar to Example 7 except that the fluorine-containing copolymer used was prepared as described by Example 3 of U.S. Pat. No. 5,285,002 (Grootaert).

Comparative Example C4

In Comparative Example C4, a curable composition was made in a manner similar to Comparative Example C1 except that the fluorine-containing copolymer used was prepared as described by Example 3 of U.S. Pat. No. 5,285,002 (Grootaert).

Injection Molding Evaluations were performed and evaluated as described above with a rating of 0 (worst release) to a rating of 8 (best release):

TABLE 5

| Mold Release Performance | |
|---|---|
| Example | Mold Release Rating |
| 12 | 6 |
| 13 | 8 |
| C4 | 5 |

The results in Table 5 show an improved mold release rating when using a fluorinated onium cure accelerator of the invention compared to a currently used commercial onium cure accelerator.

When comparing all of the above results in Tables 1–5, fluorinated onium cure accelerators of the invention show a combination of rapid cure rates, no loss in physical properties, and improved injection molding release properties and generally improved compression set properties relative to the Comparative Examples evaluated.

Examples 14–18

Curable Elastomer Mixtures of 70.2% Fluorine Terpolymers:

In Example 14, a curable composition of the invention was made and evaluated as in Example 7 except 100 g of a fluorine-containing terpolymer was used instead of Fluorel™ fluoroelastomer FC-2145. The specific terpolymer used was made as described in Example 5 of U.S. Pat. No. 5,285,002 (Grootaert). Also, 0.42 g (1.25 mmhr) of bisphenol-AF was reacted with the fluorinated onium cure accelerator by reacting the fluorinated phosphonium chloride (prepared as Example 1) with the sodium salt of bisphenol AF (prepared as described in Example 22 of U.S. Pat. No. 4,912,171 (Grootaert et al)).

The acid acceptors and carbon black listed in Table 6, below, were mixed on a two-roll mill with the bisphenol-AF-onium reaction product and the fluorine-containing terpolymer. Amounts of the reagents are in parts per hundred rubber, (phr) or mmoles per hundred parts rubber, (mmhr). An additional 1.68 g (5.0 mmhr) bisphenol-AF was added to the mixture on the two-roll mill as an ethanol solution such that the final amount of bisphenol-AF was 2.1 pphr.

TABLE 6

| 70.2% F terpolymer Reaction product | 100 g | |
|---|---|---|
| bisphenol-AF | 0.42 g | 1.25 mmhr |
| NaOCH$_3$ (30% solids) | 0.23 g | 1.25 mmhr |
| Fluorinated Onium | | 1.25 mmhr |
| Additional bisphenol-AF | 1.68 g | 5.0 mmhr |
| Ca(OH)$_2$ | 6 g | |
| MgO | 3 g | |
| Carbon black MT | 30 g | |

The cure rheology results of testing the terpolymer curable composition of the present invention are shown in Table 7. Mechanical property data were obtained from press-cured and post-cured sheets, heated for 15 min at 177° C. and 16 hrs at 232° C., respectively. Data are listed in Tables 8 and 9.

In Examples 15–18, curable compositions of the invention were made in a similar manner to Example 14 except using the onium cure accelerators made as Examples 8–11, respectively. Data are reported in Tables 8 and 9.

Comparative Examples C5–C7

In Comparative Example C5, a curable composition was made and evaluated in a manner similar to Example 14 except the onium cure accelerator used was tributyl methoxy propyl phosphonium chloride, prepared as described in Example 16 of U.S. Pat. No. 4,912,171 (Grootaert et al).

In Comparative Example C6, a curable composition was made and evaluated in a manner similar to Example 14 except the onium cure accelerator used was the fluoroalkyl amide onium described in comparative example C2.

In Comparative Example C7, a curable composition was made and evaluated in a manner similar to Example 14 except the onium cure accelerator used was the fluoroalkyl amide onium described in comparative example C3.

TABLE 7

| Example | (dN · m) $M_L$ | (dN · m) $M_H$ | (dN · m) ΔT | (min.) $t_s2$ | (min.) t'50 | (min.) t'90 |
|---|---|---|---|---|---|---|
| 14 | 0.76 | 23.7 | 22.9 | 1.45 | 1.75 | 2.27 |
| 15 | 1.46 | 30.7 | 29.3 | 2.81 | 3.73 | 4.75 |
| 16 | 1.46 | 31.6 | 30.1 | 2.82 | 3.82 | 4.9 |
| 17 | 1.33 | 31.0 | 29.7 | 2.05 | 2.61 | 3.27 |
| 18 | 1.16 | 29.3 | 28.1 | 2.63 | 3.53 | 4.77 |
| C5 | 1.85 | 27.6 | 25.7 | 1.96 | 2.62 | 3.74 |
| C6 | 1.31 | 29.3 | 28.0 | 3.92 | 5.83 | 8.73 |
| C7 | 1.31 | 22.6 | 21.3 | 4.34 | 8.43 | 20.36 |

The data in Table 7 indicate a similar or more rapid cure when using onium cure accelerators of the present invention relative to the Comparative Examples.

TABLE 8

| Press-Cured Sheet Mechanical Property Data | | | |
|---|---|---|---|
| Example | Stress at 100% Elong. (MPa) | Elongation at Break (%) | Tensile Strength (MPa) |
| 14 | 4.1 | 290 | 10.2 |
| 15 | 3.6 | 309 | 8.6 |
| 16 | 3.7 | 287 | 8.3 |
| 17 | 3.6 | 224 | 8.4 |
| 18 | 4.1 | 254 | 8.5 |
| C5 | 3.2 | 341 | 8.6 |
| C6 | 3.9 | 315 | 9.4 |
| C7 | 2.7 | 536 | 7.3 |

The results in Table 8 show that the curable compositions of this invention provide cured articles with acceptable initial cure properties.

TABLE 9

| Post-Cure Sheet Mechanical Property Data | | | |
|---|---|---|---|
| Example | Stress at 100% Elong. (MPa) | Elongation at Break (%) | Tensile Strength (MPa) |
| 14 | 5.5 | 219 | 13.7 |
| 15 | 4.8 | 290 | 13.0 |
| 16 | 5.2 | 253 | 12.6 |
| 17 | 5.2 | 213 | 13.1 |

TABLE 9-continued

Post-Cure Sheet Mechanical Property Data

| Example | Stress at 100% Elong. (MPa) | Elongation at Break (%) | Tensile Strength (MPa) |
|---|---|---|---|
| 18 | 6.1 | 192 | 13.9 |
| C5 | 3.8 | 254 | 11.1 |
| C6 | 5.7 | 246 | 13.9 |
| C7 | 3.8 | 422 | 10.2 |

The results in Table 9 show the curable compositions of this invention provide cured articles with acceptable post cure properties.

Compression set data were obtained using ASTM method D-395-89. O-rings were press cured for 12 min. at 177° C. and post cured for 16 hrs at 232° C. O-rings were compressed 25% for 70 hrs at 200° C. Data (shown in Table 10) are reported as percent of the compression remaining after the tests.

TABLE 10

| Example | Comp set (%) |
|---|---|
| 14 | 15.7 |
| 15 | 20.1 |
| 16 | 20.1 |
| 17 | 21.7 |
| 18 | 19.1 |
| C5 | 22 |
| C6 | 24.1 |
| C7 | 52.5 |

The results in Table 10 show the curable compositions of this invention provide cured articles with improved compression set properties.

The mold release performance of compositions prepared according to Examples 14–18 and C5–C7 was evaluated as well. The results are reported in Table 11.

TABLE 11

Mold Release Performance of Terpolymer Examples of the Present Invention:

| Example | Mold Release Rating |
|---|---|
| 14 | 6 |
| 15 | 7 |
| 16 | 6 |
| 17 | 6 |
| 18 | 7 |
| C5 | 5 |
| C6 | 5 |
| C7 | 0 |

The results in Table 11 show an improved mold release rating when using a fluorinated onium cure accelerator of the invention compared to other onium cure accelerators.

When comparing all of the results set forth in Tables 7–11, fluorinated onium cure accelerators of the invention show a combination of rapid cure rates, no loss in physical properties, and improved injection molding release properties and generally improved compression set properties relative to the Comparative Examples evaluated.

Other embodiments are within the following claims.

We claim:

1. A compound having the formula:

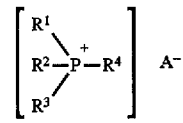

where $A^-$ is a counterion; $R^1$, $R^2$, $R^3$, and $R^4$, independently, comprise (a) a non-fluorinated alkyl, cycloalkyl, allyl, aryl, or aralkyl group; (b) an onium-containing group; or (c) a group having the formula —$(CH_2)_n$—Y—$R^5$ in which n is at least two; Y is a spacer arm comprising a —$CH_2$—, —O—, —$OCH_2$—, —S—, —$SO_2$—, or —Z—$SO_2$— group; Z is an —$R^6$—O—, —$N(R^7)$—, or —N(H)— group; $R^6$ is a substituted or unsubstituted phenylene group; $R^7$ is H or a non-fluorinated alkyl, cycloalkyl, allyl, aryl, or alkaryl group; and $R^5$ is a fluorinated group, perfluorinated group, or combination thereof, with the proviso that (i) at least one of $R^1$, $R^2$, $R^3$, and $R^4$ comprises a group having the formula —$(CH_2)_n$—Y—$R^5$; and (ii) the total number of fluorine atoms in said compound is at least 5.

2. A compound according to claim 1 wherein at least one of said $R^1$, $R^2$, $R^3$, and $R^4$ groups comprises an alkyl group having at least four carbon atoms.

3. A compound according to claim 1 wherein at least one of said $R^1$, $R^2$, $R^3$, and $R^4$ groups comprises a group having the formula —$(CH_2)_n$—O—$R^5$.

4. A compound according to claim 1 wherein at least one of said $R^1$, $R^2$, $R^3$, and $R^4$ groups comprises a group having the formula —$(CH_2)_n$—Ph-O—$SO_2$—$R^5$.

5. A compound according to claim 1 wherein said $R^5$ group is a perfluorinated alkyl group.

6. A compound according to claim 1 wherein said $R^5$ group is a perfluorinated ether group having the formula:

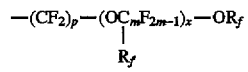

in which p is greater than or equal to zero with the proviso that when Y is —O— p is greater than or equal to one, m is greater than or equal to one, x is greater than or equal to two, $R_f$ is a perfluoroalkyl group, and $R'_f$ is F or a perfluoroalkyl group.

7. A compound according to claim 1 wherein said $R^5$ group is a fluorinated alkyl group having the formula —$CH_2$—$(CF_2)_x$—H in which x is at least four.

8. A compound according to claim 1 having the formula:

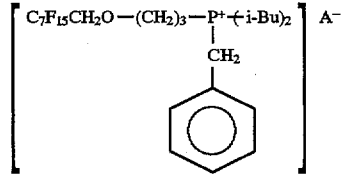

9. A compound according to claim 1 having the formula:
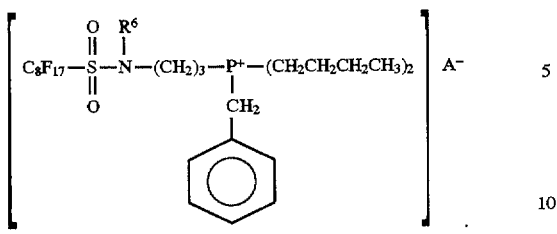
10. A compound according to claim 1 having the formula:
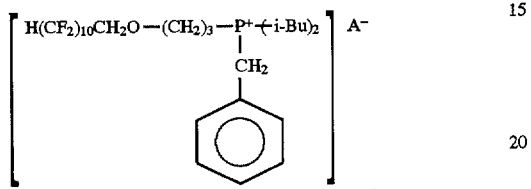
11. A compound according to claim 1 having the formula:
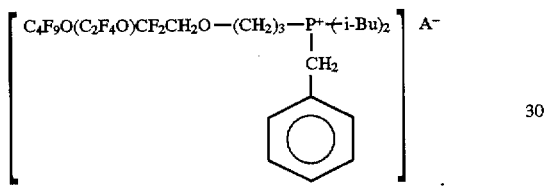
12. A compound according to claim 1 having the formula:
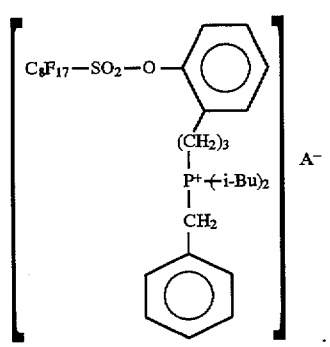
13. A compound according to claim 1 having the formula:
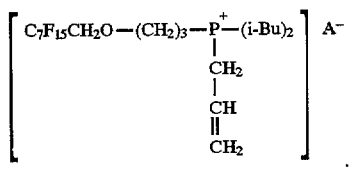
* * * * *

UNITED STATES PATENT AND TRADEMARK OFFICE
CERTIFICATE OF CORRECTION

PATENT NO.: 5,734,085

DATED: March 31, 1998

INVENTOR(S): William D. Coggio, Richard M. Flynn, George G. Moore

It is certified that error appears in the above-identified patent and that said Letters Patent is hereby corrected as shown below:

Col. 18, line 45, "$-(CF_2)_p-(O\underset{R_f}{C}_mF_{2m-1})_x-OR_f$" should read $--(CF_2)_p-(O\underset{R_{f'}}{C}_mF_{2m-1})_x-OR_f--$ Signed and Sealed this Eleventh Day of May, 1999

Attest:

Q. TODD DICKINSON

Attesting Officer

Acting Commissioner of Patents and Trademarks